United States Patent
Kubota et al.

[11] Patent Number: 6,004,902
[45] Date of Patent: Dec. 21, 1999

[54] TRIAZINE DERIVATIVES

[75] Inventors: Mineyuki Kubota; Masatoshi Saitou, both of Sodegaura; Kazuyoshi Koike, Ichihara; Shin-ichiro Ogawa, Sodegaura, all of Japan

[73] Assignee: Idemitsu Kosan Co., Ltd., Tokyo, Japan

[21] Appl. No.: 08/875,786

[22] PCT Filed: Feb. 19, 1996

[86] PCT No.: PCT/JP96/00360

§ 371 Date: Oct. 27, 1997

§ 102(e) Date: Oct. 27, 1997

[87] PCT Pub. No.: WO96/25404

PCT Pub. Date: Aug. 22, 1996

[30] Foreign Application Priority Data

Feb. 17, 1995 [JP] Japan .................................. 7-029124

[51] Int. Cl.[6] .......................... C07D 251/18; A01N 43/68
[52] U.S. Cl. ............................................. 504/234; 544/206
[58] Field of Search ............................. 544/206; 504/234

[56] References Cited

U.S. PATENT DOCUMENTS 5,250,686  10/1993  Adachi et al. .......................... 544/206

FOREIGN PATENT DOCUMENTS

| | | |
|---|---|---|
| 5-320145 | 12/1993 | Japan . |
| 6-298745 | 10/1994 | Japan . |
| 7-76504 | 3/1995 | Japan . |
| 7-82107 | 3/1995 | Japan . |
| 7-39400 | 5/1995 | Japan . |
| 7-267805 | 10/1995 | Japan . |

*Primary Examiner*—John M. Ford
*Attorney, Agent, or Firm*—Frishauf, Holtz, Goodman, Langer & Chick, P.C.

[57] ABSTRACT

A triazine compound of the formula (I),

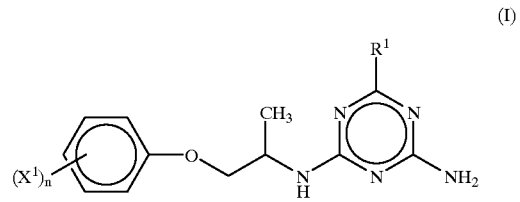

wherein $X^1$ is a linear or branched $C_1$–$C_4$ alkyl group or a halogen atom; n is an integer of 0 or 1 to 4, provided that when n is 2 or more, a plurality of substituents $X^1$ are the same or different; and $R^1$ is a linear or branched $C_1$–$C_{10}$ alkyl group which is optionally substituted with 1 to 4 $C_1$–$C_4$ alkoxy groups and/or hydroxy groups, provided that when the linear or branched $C_1$–$C_{10}$ alkyl group is substituted with 2 or more $C_1$–$C_4$ alkoxy groups and/or hydroxy groups, a plurality of the $C_1$–$C_4$ alkoxy groups and/or hydroxy groups are the same or different; a process for the production thereof, and a herbicide composition containing the compound. The triazine compounds exhibit excellent crops-weeds selectivity, even under poor conditions of excessive water content, etc., which are liable to cause phytotoxicity.

14 Claims, No Drawings

TRIAZINE DERIVATIVES

This application is the United States national application under 35 USC 371 of the International application PCT/JP96/00360 filed Feb. 19, 1996,

TECHNICAL FIELD

The present invention relates to a novel triazine derivative, a process for the production thereof, and a herbicide containing the same as an active ingredient.

TECHNICAL BACKGROUND

Triazine derivatives described in International Laid-open Publication WO90/09378 to Applicant are safe to gramineous crops, rice in particular, in both post-emergence treatment and pre-emergence treatment and exhibit high herbicidal efficacy against weeds which are hard to control. The general formula of the basic structure of the triazine derivative described in the above Publication is as follows.

(Basic structure A)

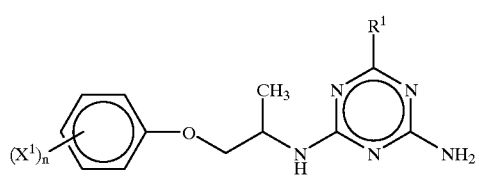

(A)

wherein $X^1$ is methyl, trifluoromethyl, methoxy or a fluorine atom, n is an integer of 0, 1 or 2, and $R^1$ is haloalkyl.

The above herbicides having high crops-weeds selectivity can control weeds without causing phytotoxicity on crops in general use, while they sometimes cause phytotoxicity due to various factors such as weather, environment and erroneous use. In particular, growth-inhibiting (particularly, root-inhibiting) herbicides are liable to cause phytotoxicity under conditions of an excessive water content. It is therefore desired to develop a herbicide which can control weeds without causing phytotoxicity on crops under such bad conditions and which have higher crops-weeds selectivity.

It is an object of the present invention to develop a novel triazine derivative having high crops-seeds selectivity under bad conditions such as conditions of an excessive water content which are liable to induce phytotoxicity, i.e., having safety to gramineous crops under conditions which are liable to induce phytotoxicity and having high herbicidal efficacy against weeds which are hard to control.

DISCLOSURE OF THE INVENTION

The present inventors have made diligent studies for achieving the above object and have found that the crops-weeds selectivity can be remarkably improved by changing the $R^1$ of a triazine derivative of the above base structure A from the haloalkyl group to an alkyl group on which an alkoxy group and/or a hydroxyl group may be substituted. The present invention has been accordingly completed.

That is, the first gist of the present invention consists in a triazine derivative of the general formula (I),

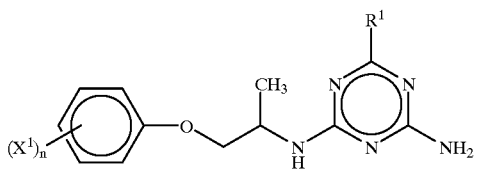

(I)

wherein $X^1$ is a linear or branched $C_1$~$C_4$ alkyl group or a halogen atom, n is an integer of 0 or 1 to 4, provided that when n is 2 or more, a plurality of substituents $X^1$ may be the same or different, and $R^1$ is a linear or branched $C_1$~$C_{10}$ alkyl group which may be substituted with 1 to 4 $C_1$~$C_4$ alkoxy groups and/or hydroxy groups, provided that when the linear or branched $C_1$~$C_{10}$ alkyl group is substituted with 2 or more $C_1$~$C_4$ alkoxy groups and/or hydroxy groups, a plurality of the $C_1$~$C_4$ alkoxy groups and/or hydroxy groups may be the same or different, or salt thereof (to be referred to as "triazine derivative (I)" hereinafter).

Further, the second gist of the present invention consists in a process for the production of a triazine derivative of the general formula (I),

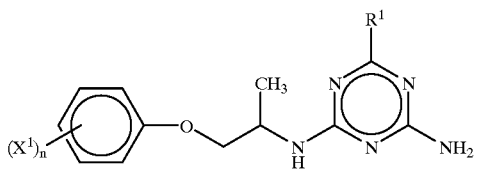

(I)

(wherein $X^1$ is a linear or branched $C_1$~$C_4$ alkyl group or a halogen atom, n is an integer of 0 or 1 to 4, provided that when n is an integer of 2 or more, a plurality of substituents $X^1$ may be the same or different, and $R^1$ is a linear or branched $C_1$~$C_{10}$ alkyl group which may be substituted with 1 to 4 alkoxy groups and/or hydroxy groups provided that when the above linear or branched $C_1$~$C_{10}$ alkyl group is substituted with 2 or more $C_1$~$C_4$ alkoxy groups and/or hydroxyl groups, a plurality of the $C_1$~$C_4$ alkoxy groups and/or hydroxy groups may be the same or different), which process comprises reacting a salt of alkylbiguanide (to be referred to as "alkylbiguanide salt (II)" hereinafter) of the general formula (II),

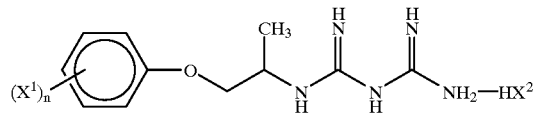

(II)

(wherein $X^1$ and n are as defined above and $X^2$ is a halogen atom), with an ester (to be referred to as "ester (III)" hereinafter) of the general formula (III), $$R_1 \; COOR^2 \quad \text{(II)}$$

(wherein $R^1$ is as defined above and $R^2$ is a $C_1$~$C_4$ alkyl group).

Further, the third gist of the present invention consists in a herbicide containing, as an active ingredient, the triazine derivative (I) which is the first gist of the present invention.

Further, the fourth gist of the present invention consists in a method of controlling weeds, which comprises applying a herbicidally effective amount of the triazine derivative (I), the first gist of the present invention, in the form of its own or together with an adjuvant.

PREFERRED EMBODIMENT FOR WORKING THE INVENTION

The triazine derivative (I) in which the first gist of the present invention consists is a compound of the following general formula (I) or a salt thereof.

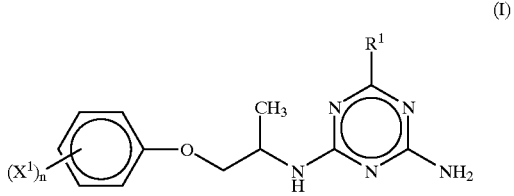

(I)

In the above general formula (I), $X^1$ is a linear or branched $C_1$~$C_4$ alkyl group or a halogen atom.

When $X^1$ is a linear or branched $C_1$~$C_4$ alkyl group, specific examples thereof include methyl, ethyl, n-propyl, i-propyl, n-butyl, i-butyl, sec-butyl, tert-butyl, cyclopropyl and cyclobutyl. Methyl is preferred.

When $X^1$ is a halogen atom, specific examples of the halogen atom include chlorine, bromine, fluorine and iodine, and fluorine is preferred.

$X^1$ may be substituted on any one of the 2- to 6-positions of the benzene ring, and preferably substituent(s) $X^1$ is substituted on the 3-position and/or the 5-position.

In the above general formula (I), n is an integer of 0 or 1 to 4, preferably 0, 1 or 2.

When n is an integer of 2 or more, a plurality of substituents $X^1$ may be the same or different.

In the above general formula (I), $R^1$ is a linear or branched $C_1$~$C_{10}$ alkyl group which may be substituted with 1 to 4 alkoxy groups and/or hydroxy groups.

When $R^1$ is a non-substituted linear or branched $C_1$~$C_{10}$ alkyl group, which is not substituted with $C_1$~$C_4$ alkoxy group or hydroxy group, specific examples of the non-substituted linear or branched $C_1$~$C_{10}$ alkyl group include, in addition to the $C_1$~$C_4$ alkyl group explained with regard to the above $X^1$, n-pentyl, i-pentyl, sec-pentyl, tert-pentyl, n-hexyl, i-hexyl, sec-hexyl, tert-hexyl, n-heptyl, i-heptyl, sec-heptyl, tert-heptyl, n-octyl, i-octyl, sec-octyl, tert-octyl, n-nonyl, i-nonyl, sec-nonyl, tert-nonyl, n-decyl, i-decyl, sec-decyl, tert-decyl, cyclopropyl, cyclobutyl, cyclopentyl, cyclohexyl and cycloheptyl. Preferred are methyl, ethyl, n-propyl, i-propyl, sec-butyl, tert-butyl, i-butyl, n-pentyl and cyclohexyl.

When $R^1$ is a $C_1$~$C_{10}$ alkyl group substituted with $C_1$~$C_4$ alkoxy group and/or hydroxy group, specific examples of the substituent $C_1$~$C_4$ alkoxy group include methoxy, ethoxy, n-propoxy, i-propoxy, n-butoxy, i-butoxy and tert-butoxy. Preferred are methoxy and tert-butoxy.

When $R^1$ is a $C_1$~$C_{10}$ alkyl group substituted with at least two $C_1$~$C_4$ alkoxy groups and/or hydroxy groups, a plurality of the substituents $C_1$~$C_4$ alkoxy groups and/or hydroxy groups may be the same or different.

When $R^1$ is a $C_1$~$C_{10}$ alkyl group substituted with 1 to 4 $C_1$~$C_4$ alkoxy groups and/or hydroxyl groups, specific examples of the $C_1$~$C_{10}$ alkyl group substituted with 1 to 4 $C_1$~$C_4$ alkoxy groups and/or hydroxyl groups include $CH_3OCH_2-$, $CH_3OC_2H_4-$, $CH_3OC_3H_6-$, $CH_3OC_4H_8-$, $C_2H_5OCH_2-$, $C_2H_5OC_2H_4-$, $C_2H_5OC_3H_6-$, $C_2H_5OC_4H_8-$, $C_2H_5OC_5H_{10}-HOCH_2-$, $HOC_2H_4-$, $HOC_3H_6-$, $HOC_4H_8-(CH_3O)_2CH-$, $(CH_3O)_2C_2H_3-$, $(CH_3O)_2C_3H_5-$, $(CH_3O)_2C_4H_7-$, $CH_3(OCH_3)CH-$, $C_2H_5(OCH_3)CH-$, $CH_3OCH_2(CH_3)CH-$, $CH_3O(CH_3)_2C-$, $(CH_3)_3C-$, $CH_2OH(CH_3)_2C-$, $(CH_3)_2COH-$, $C_2H_5(OH)CH-$, methyl-substituted cyclopropyl, methyl-substituted cyclobutyl, methyl-substituted cyclopentyl, methyl-substituted cyclohexyl, ethyl-substituted cyclopentyl, and ethyl-substituted cyclohexyl.

$R^1$ is preferably a linear or branched $C_1$~$C_8$ alkyl group which may be substituted with 1 to 4 $C_1$~$C_4$ alkoxy groups and/or hydroxy groups. More preferably, $R^1$ is a non-substituted linear or branched $C_1$~$C_8$ alkyl group, a linear or branched $C_1$~$C_4$ alkyl group substituted with 1 or 2 $C_1$~$C_4$ alkoxy groups or a linear or branched $C_1$~$C_4$ alkyl group substituted with one hydroxy group. Furthermore preferably, $R^1$ is a linear or branched $C_1$~$C_4$ alkyl group or a cycloalkyl group substituted with 1 or 2 methoxy groups, one butoxy group or one hydroxy group.

The triazine derivative of the general formula (I) in the present invention has optical isomers, and it is generally obtained as a racemic modification, while one alone of antipodes can be obtained by a known method such as asymmetric synthesis. The triazine derivative (I) of the present invention exhibits herbicidal activity even if it is a racemic modification or an optical isomer alone. The triazine derivative (I) of the present invention includes the above racemic modification and the above optical isomers. Further, the triazine derivative (I) of the present invention can be used as a herbicidally active ingredient even if it is in the form of a salt with an inorganic acid or an organic acid.

Examples of the acid which can form a salt with the triazine derivative of the present invention include inorganic acids such as hydrochloric acid, hydroiodic acid, hydrobromic acid, hydrofluoric acid, sulfuric acid, nitric acid and phosphoric acid, and organic acids such as acetic acid and sulfonic acids including methanesulfonic acid and toluenesulfonic acid.

The process for the production of a triazine derivative, in which the second gist of the present invention consists, is represented by the reaction scheme,

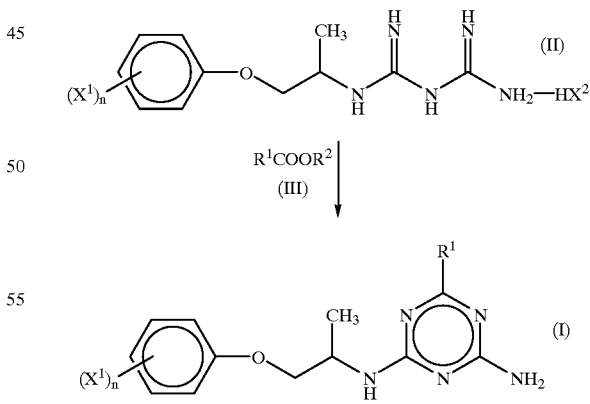

(wherein $X^1$, n and $R^1$ are as defined in the above triazine derivative (I), $X^2$ is a halogen atom, and $R^2$ is a $C_1$~$C_4$ alkyl group). An alkylbiguanide salt (II) is reacted with an ester (III) to form a triazine ring, whereby the intended triazine derivative is obtained.

The above reaction is preferably carried out in the presence of a catalyst. Examples of the catalyst that can be used in the present invention include alkoxides such as sodium methoxide, sodium ethoxide and magnesium diethoxide; inorganic bases such as sodium phosphate, potassium carbonate, sodium hydroxide and potassium hydroxide; and inorganic bases such as 1,8-diazabicyclo[5,4,0]-7-undecene (DBU), 1,5-diazabicyclo[4,3,0]-5-nonen (DBN), triethylamine and pyridine. Preferred are sodium methoxide and sodium ethoxide.

The amount of the catalyst based on the alkylbiguanide salt (II) is generally 1.1 to 10 equivalent weights, preferably 1.5 to 5 equivalent weights.

The amount of the ester (III) used in the present invention is generally 1 to 10 equivalent weights, preferably 1 to 5 equivalent weights, based on the alkylbiguanide salt (II).

The above reaction is preferably carried out in the presence of a solvent, and the solvent that can be used in the above reaction is selected, for example, from alcohols such as methanol, ethanol and isopropanol; ketones such as acetone, methyl ethyl ketone and cyclohexanone; aliphatic hydrocarbons such as n-hexane, n-heptane and n-decane; cyclic hydrocarbons such as benzene, decalin and alkylnaphthalene; chlorinated hydrocarbons such as carbon tetrachloride, methylene dichloride, chlorobenzene and dichlorobenzene; and ethers such as tetrahydrofuran and dioxane. Alcohols are preferred, and methanol and ethanol are particularly preferred.

In the present invention, a dehydrating agent may be used for preventing the hydrolysis of the ester (III). Examples of the dehydrating agent that can be used in the process of the present invention include molecular sieve, anhydrous calcium sulfate, anhydrous sodium sulfate, sodium carbonate, calcium oxide, aluminum oxide, magnesium sulfate, potassium carbonate and barium oxide. Molecular sieve and anydrous sodium sulfate are particularly preferred. The amount of the dehydrating agent is 10 to 200% by weight, preferably 50 to 100% by weight, based on the alkylbiguanide salt (II).

The reaction temperature of the above reaction is generally −10 to 150° C., preferably −10 to 120° C. The reaction time is generally 2 to 30 hours, preferably approximately 7 to 15 hours.

After the completion of the reaction, the reaction mixture is poured in water, and the end product is extracted with an organic solvent such as ethyl acetate. The resultant organic layer is dehydrated with a dehydrating agent such as anhydrous sodium sulfate, and then the organic solvent is removed by means of distillation under reduced pressure, and the like. The resultant residue is purified by means of silica gel column chromatography, etc., whereby the intended triazine derivative can be isolated in the form of a crystal.

The herbicide containing, as an active ingredient, the triazine derivative or a salt thereof, which is the third gist of the present invention, will be explained below.

The herbicide of the present invention contains, as an essential ingredient, the novel triazine derivative of the general formula (I) or a salt thereof provided by the present invention. The compound provided by the present invention is mixed with a liquid carrier such as a solvent or a solid carrier such as a mineral fine powder, and the mixture can be prepared into the form of a wettable powder, an emulsifiable concentrate, a dust, granules, or the like. For imparting the preparation with emulsifiability, dispersibility and spreadability, a surfactant can be added.

When the herbicide of the present invention is used in the form of a wettable powder, generally, a composition is prepared by mixing 10 to 55% by weight of the triazine derivative (I) of the present invention, 40 to 88% by weight of a solid carrier and 2 to 5% by weight of a surfactant, and the composition can be used as a wettable powder.

Further, when it is used in the form of an emulsifiable concentrate, generally, it can be prepared by mixing 20 to 50% by weight of the triazine derivative (I) of the present invention, 35 to 75% by weight of a solvent and 5 to 15% by weight of a surfactant.

Further, when the herbicide of the present invention is used in the form of a dust, generally, it can be prepared by mixing 1 to 15% by weight of the trizaine derivative (I) of the present invention, 80 to 97% by weight of a solid carrier and 2 to 5% by weight of a surfactant.

Further, when it is used in the form of granules, it can be prepared by mixing 1 to 15% by weight of the triazine derivative (I) of the present invention, 80 to 97% by weight of a solid carrier and 2 to 5% by weight of a surfactant.

The above solid carrier can be selected from mineral fine powders, and examples of the mineral fine powders include oxides such as diatomaceous earth and slaked lime, phosphates such as apatite, sulfates such as gypsum, and silicates such as talc, pyroferrite, clay, kaolin, bentonite, acid clay, white carbon, powdered quartz and powdered silica.

The solvent is selected from organic solvents. Specific examples of the solvent include aromatic hydrocarbons such as benzene, toluene and xylene, chlorinated hydrocarbons such as o-chlorotoluene, trichloroethane and trichloroethylene, alcohols such as cyclohexanol, amyl alcohol and ethylene glycol, ketones such as isophorone, cyclohexanone and cyclohexenyl-cyclohexanone, ethers such as butyl cellosolve, diethyl ether and methyl ethyl ether, esters such as isopropyl acetate, benzyl acetate and methyl phthalate, amides such as dimethylformamide, and mixtures of these.

Further, the surfactant can be selected from anionic, nonionic, cationic and amphoteric ones (amino acid and betaine).

The herbicide of the present invention may be used as a mixture with any one of insecticides, bactericides, plant growth regulators and fertilizers.

The herbicide of the present invention may be in the form of a neat liquid, and in this case, end users can dilute it as required for use.

The method of controlling weeds, which comprises applying a herbicidally effective amount of the triazine derivative (I) or a salt thereof, provided by the present invention, in the form of its own or together with an adjuvant, which method is the fourth gist of the present invention, will be explained below.

The above adjuvant refers to a substance which does not have any herbicidal activity itself and is added to the triazine derivative (I) of the present invention for preparing the herbicide of the present invention in the form of a wettable powder, an emulsifiable concentrate, a dust, granules, or the like, and which imparts these preparations with emulsifiability, dispersibility and spreadability.

The application comprises treating a plant-growing site with the above triazine derivative, its salt or is optical isomer of the present invention or the above herbicide containing any one of these compounds, provided by the present invention, before or after the germination of weeds.

The means of the application differs depending upon plants and use environments, while it may be, for example, spraying, water spraying, diffusing or showering.

The method of controlling weeds, provided by the present invention, is useful in the planting of gramineous crops such as rice, wheat, barley, corn, oat and sorghum and broadleaved crops such as soybean, cotton, beet, sunflower and rapeseed, and it is also effective for orchard, vegetables such as fruit vegetables, root vegetables and leaf vegetables and lawn.

The herbicide of the present invention is useful for controlling weeds such as Persian speedwell, violet, knotweed, cleavers, wild chamomile, dead nettle, corn poppy, blackgrass, annual bluegrass, wild oat, velvetleaf, cocklebur, morning glory, common lamsquaters, slender amaranth, jimsonweed, black nightshade, green foxtail, large crabgrass, shattercane, elatine triandra, monochoria, toothcup, false pimpernel, barnyardgrass, bulrush, umbrella plant, needle-upright-clubrush, cyperus serotinus, sigettaria pygmaea and arrowhead.

EXAMPLES

The present invention will be specifically explained with reference to Examples and Herbicide Examples hereinafter, while the present invention shall not be limited thereto.

Example 1

5.00 Grams (16.7 mmol) of 2-(3',5'-dimethylphenoxy) isopropylbiguanide hydrochloride (corresponding to alkylbiguanide salt (II)) synthesized by the method described in JP-A-63-264465 was dissolved in 30 ml of anhydrous methanol, and 4.5 g of a molecular sieve 3A as a dehydrating agent was added thereto. While the mixture was stirred at −10° C., 1.80 g (33.4 mmol) of sodium methoxide as a base was added, and further, 1.47 g (16.7 mmol) of methyl propionate (corresponding to ester (III)) was dropwise added. The mixture was stirred for 12 hours, and the molecular sieve 3A was filtered off, and a mother liquor was concentrated with an evaporator. To the resultant residue were added 50 ml of ethyl acetate and 50 ml of water, to separate the mixture. An ethyl acetate layer was washed with water and dried over anhydrous sodium sulfate, and the solvent was distilled off with an evaporator. The residue was purified by silica gel column chromatography (developer solvent: hexane/ethyl acetate=1/1) to give 4.27 g (yield 85%) of an intended 2-amino-4-[2-(3',5'-dimethylphenoxy)isopropylaminol]-6-ethyl-1,3,5-triazine. Table 2 shows NMR and IR data of the obtained triazine compound.

Example 2

5.00 Grams (16.7 mmol) of 2-(3',5'-dimethylphenoxy) isopropylbiguanide hydrochloride (corresponding to alkylbiguanide salt (II)) synthesized by the method described in JP-A-63-264465 was dissolved in 30 ml of anhydrous methanol. While the resultant solution was stirred at −10° C., 1.80 g (33.4 mmol) of sodium methoxide as a base was added, and further, 1.47 g (16.7 mmol) of ethyl acetate (corresponding to ester (III)) was dropwise added. The mixture was stirred for 12 hours, then, a precipitate was filtered off, and a mother liquor was concentrated with an evaporator. To the resultant residue were added 50 ml of ethyl acetate and 50 ml of water, to separate the mixture. An ethyl acetate layer was washed with water and then dried over anhydrous sodium sulfate, and the solvent was distilled off with an evaporator. The residue was purified by silica gel column chromatography (developer solvent: hexane/ethyl acetate=1/1) to give 3.45 g (yield 72%) of an intended 2-amino-4-[2-(3',5'-dimethylphenoxy) isopropylamino]-6-methyl-1,3,5-triazine. Table 2 shows NMR and IR data of the obtained triazine compound.

Examples 3–5 and 7 to 18

Reactions were carried out in the same manner as in Example 1 except that the methyl propionate (corresponding to ester (III)) used in Example 1 was replaced with esters shown in Table 1. Table 1 shows esters used and structures and reaction yields of triazine compounds obtained. Table 2 shows NMR and IR data of the obtained triazine compounds.

Example 6

With stirring at room temperature, 9.66g (50.1 mmol) of a solution of 28% of sodium methoxide as a base in methanol was added to 5.00 g (16.7 mmol) of 2-(3',5'-dimethylphenoxy)isopropylbiguanide hydrochloride (corresponding to alkylbiguanide salt (II)) synthesized by the method described in JP-A-63-264465. Further, 5.82 g (50.1 mmol) of methyl trimethylacetate (corresponding to ester (III)) was dropwise added. The reaction mixture was refluxed under heat for 7 hours, a precipitate was filtered off, and a filtrate was concentrated with an evaporator. To the resultant residue were added 50 ml of ethyl acetate and 50 ml of water, to separate the mixture. An ethyl acetate layer was washed with water and then dried over anhydrous sodium sulfate, and the solvent was distilled off with an evaporator. The residue was purified by silica gel column chromatography (developer solvent: hexane/ethyl acetate= 1/1) to give 4.94 g (yield 90%) of an intended 2-amino-4-[2-(3',5'-dimethylphenoxy)isopropylamino]-6-tert-butyl-1,3,5-triazine. Table 2 shows NMR and IR data of the obtained triazine compound.

Example 19

With stirring at room temperature, 11.5 g (59.7 mmol) of a solution of 28% of sodium methoxide as a base in methanol was added to 5.00 g (19.9 mmol) of 2-(3'-fluorophenoxy)isopropylbiguanide hydrochloride (corresponding to alkylbiguanide salt (II)) synthesized by the method described in JP-A-63-264465. Further, 6.93 g (59.7 mmol) of methyl trimethylacetate (corresponding to ester (III)) was dropwise added. The reaction mixture was refluxed under heat for 7 hours, a precipitate was filtered off, and a filtrate was concentrated with an evaporator. To the resultant residue were added 50 ml of ethyl acetate and 50 ml of water, to separate the mixture. An ethyl acetate layer was washed with water and then dried over anhydrous sodium sulfate, and the solvent was distilled off with an evaporator. The residue was purified by silica gel column chromatography (developer solvent: hexane/ethyl acetate= 1/1) to give 4.77 g (yield 85%) of an intended 2-amino-4-[2-(3'-fluorophenoxy)isopropylamino]-6-tert-butyl-1,3,5-triazine. Table 2 shows NMR and IR data of the obtained triazine compound.

Examples 20 and 21

Reactions were carried out in the same manner as in Example 19 except that the methyl timethylacetate (corresponding to ester (III)) used in Example 19 was replaced with esters shown in Table 1. Table 5 shows esters used and structures and reaction yields of triazine compounds obtained. Table 2 shows NMR and IR data of the obtained triazine compounds.

Examples 22 and 23

Reactions were carried out in the same manner as in Example 19 except that the 2-(3'-fluorophenoxy) isopropylguanide hydrochloride (corresponding to alkylbiguanide salt (II)) used in Example 19 was replaced with biguanide hydrochlorides shown in Table 1. Table 1 shows the biguanide hydrochlorides used and structures and reaction yields of triazine compounds obtained. Table 2 shows NMR and IR data of the obtained triazine compounds.
TABLE 1
| Ex. No. | Ester (III) as raw material | Obtained triazine derivative (I) | Yield (%) |
|---|---|---|---|
| | | (No. 1) | |
| 1 | 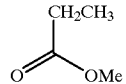 | 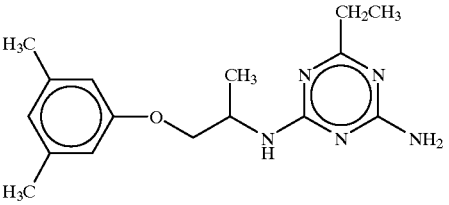 | 85 |
| 2 | 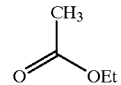 | 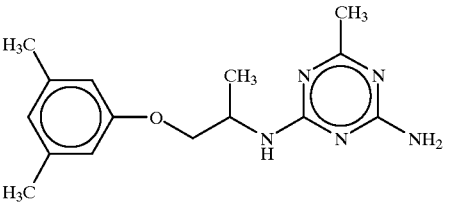 | 72 |
| 3 | 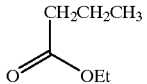 | 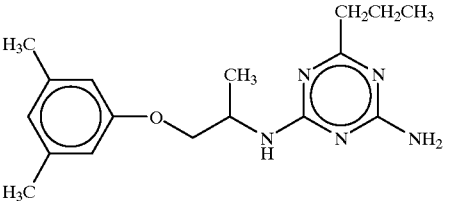 | 63 |
| 4 | 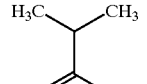 | 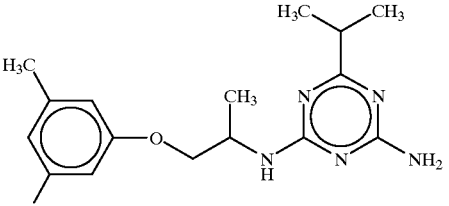 | 34 |
| 5 | 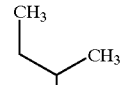 | 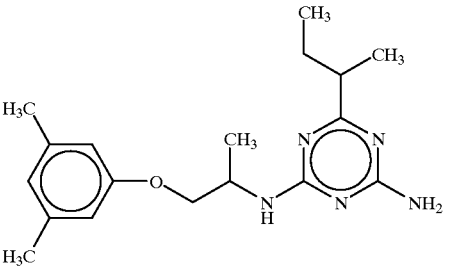 | 37 |

TABLE 1-continued

| Ex. No. | Ester (III) as raw material | Obtained triazine derivative (I) | Yield (%) |
|---|---|---|---|
| 6 | (CH3)3C-C(=O)-OMe (pivalate methyl ester) | 2-amino-4-tert-butyl-6-[N-(1-(3,5-dimethylphenoxy)propan-2-yl)amino]-1,3,5-triazine | 90 |
| 7 | (CH3)2CHCH2-C(=O)-OEt (ethyl isovalerate) | 2-amino-4-isobutyl-6-[N-(1-(3,5-dimethylphenoxy)propan-2-yl)amino]-1,3,5-triazine | 45 |
| 8 | CH3(CH2)4-C(=O)-OEt (ethyl hexanoate) | 2-amino-4-pentyl-6-[N-(1-(3,5-dimethylphenoxy)propan-2-yl)amino]-1,3,5-triazine | 90 |
| 9 | cyclohexyl-C(=O)-OMe | 2-amino-4-cyclohexyl-6-[N-(1-(3,5-dimethylphenoxy)propan-2-yl)amino]-1,3,5-triazine | 45 |
| 10 | CH3CH(OCH3)-C(=O)-OEt | 2-amino-4-(1-methoxyethyl)-6-[N-(1-(3,5-dimethylphenoxy)propan-2-yl)amino]-1,3,5-triazine | 55 |

(No. 2)

TABLE 1-continued

| Ex. No. | Ester (III) as raw material | Obtained triazine derivative (I) | Yield (%) |
|---|---|---|---|
| 11 | CH₃CH₂CH(OCH₃)C(O)OEt | 3,5-dimethylphenoxy-CH(CH₃)CH₂-NH-[4,6-diamino-triazine with CH(OCH₃)CH₂CH₃ substituent] (No. 3) | 40 |
| 12 | CH₃OCH₂CH(CH₃)C(O)OEt | corresponding triazine with -CH(CH₃)CH₂OCH₃ substituent | 41 |
| 13 | (CH₃)₂C(OCH₃)C(O)OEt | corresponding triazine with -C(CH₃)₂OCH₃ substituent | 34 |
| 14 | (CH₃)₃C-O-CH₂C(O)OEt | corresponding triazine with -CH₂-O-C(CH₃)₃ substituent | 43 |
| 15 | (CH₃O)₂CH-C(O)OMe | corresponding triazine with -CH(OCH₃)₂ substituent | 43 |

TABLE 1-continued

| Ex. No. | Ester (III) as raw material | Obtained triazine derivative (I) | Yield (%) |
|---|---|---|---|
| 16 | HOCH₂C(CH₃)₂C(O)OMe | 2-amino-4-[2-(3,5-dimethylphenoxy)-1-methylethylamino]-6-[1-hydroxymethyl-1-methylethyl]-1,3,5-triazine (No. 4) | 33 |
| 17 | (CH₃)₂C(OH)C(O)OEt | 2-amino-4-[2-(3,5-dimethylphenoxy)-1-methylethylamino]-6-[1-hydroxy-1-methylethyl]-1,3,5-triazine | 31 |
| 18 | CH₃CH₂CH(OH)C(O)OEt | 2-amino-4-[2-(3,5-dimethylphenoxy)-1-methylethylamino]-6-[1-hydroxypropyl]-1,3,5-triazine | 35 |
| 19 | (CH₃)₃CC(O)OMe | 2-amino-4-tert-butyl-6-[2-(3-fluorophenoxy)-1-methylethylamino]-1,3,5-triazine | 85 |
| 20 | CH₃C(O)OEt | 2-amino-4-[2-(3-fluorophenoxy)-1-methylethylamino]-6-methyl-1,3,5-triazine | 81 |
| 21 | cyclohexyl-C(O)OMe | 2-amino-4-cyclohexyl-6-[2-(3-fluorophenoxy)-1-methylethylamino]-1,3,5-triazine | 75 |

TABLE 1-continued

| Ex. No. | Ester (III) as raw material | Obtained triazine derivative (I) | Yield (%) |
|---|---|---|---|
| | (No. 5) | | |
| 22 | Phenoxy-CH$_2$-CH(CH$_3$)-NH-C(=NH)-NH-C(=NH)-NH$_2$·HCl | 2-(phenoxymethyl-1-methylethylamino)-4-tert-butyl-6-amino-s-triazine | 42 |
| 23 | 3-Methylphenoxy-CH$_2$-CH(CH$_3$)-NH-C(=NH)-NH-C(=NH)-NH$_2$·HCl | 2-((3-methylphenoxymethyl)-1-methylethylamino)-4-tert-butyl-6-amino-s-triazine | 39 |

Ex. = Example

TABLE 2

| Example No. | IR (cm$^{-1}$)*$^1$ S-triazine | $^1$H-NMR*$^2$ |
|---|---|---|
| | (No. 1) | |
| 1 | 1560 | 1.22(3H, t, J=8.1Hz, CH$_2$C$\underline{H}_3$), 1.32(3H, t, J=7.2Hz, CHC$\underline{H}_3$), 2.27(6H, s, ArC$\underline{H}_3$×2), 2.45(2H, q, J=8.1Hz, C$\underline{H}_2$CH$_3$), 3.80–4.05(2H, m, OC$\underline{H}_2$), 4.25–4.60(1H, m, C$\underline{H}$NH), 5.10–5.60(3H, m, N$\underline{H}$, N$\underline{H}_2$), 6.45–6.70 (3H, m, C$_6\underline{H}_3$) |
| 2 | 1575 | 1.35(3H, d, J=7.2Hz, CHC$\underline{H}_3$), 1.98(3H, s, Triazine-C$\underline{H}_3$), 2.27(6H, s, ArC$\underline{H}_3$×2), 3.75–4.10(2H, m, OC$\underline{H}_2$), 4.25–4.70(1H, m, C$\underline{H}$NH), 5.10–5.60(3H, m, N$\underline{H}$, N$\underline{H}_2$), 6.45–6.70 (3H, m, C$_6\underline{H}_3$) |
| 3 | 1550 | 0.99(3H, t, J=8.1Hz, CH$_2$C$\underline{H}_3$), 1.36(3H, d, J=7.2Hz, CHC$\underline{H}_3$), 1.50–2.00(2H, m, C$\underline{H}_2$CH$_3$), 2.29(6H, s, ArC$\underline{H}_3$×2), 2.20–2.60(2H, m, C$\underline{H}_2$CH$_2$CH$_3$) 3.70–4.10(2H, m, OC$\underline{H}_2$), 4.15–4.70 (1H, m, C$\underline{H}$NH), 5.00–5.70(3H, m, N$\underline{H}$, N$\underline{H}_2$), 6.40–6.70(3H, m, C$_6\underline{H}_3$) |
| 4*$^3$ | 1570 | 1.22(6H, d, J=7.2Hz, C$\underline{H}_3$CHC$\underline{H}_3$), 1.36(3H, d, J=7.2Hz, CHC$\underline{H}_3$) 2.28(6H, s, ArC$\underline{H}_3$×2), 2.40–2.90(1H, m, CH$_3$C$\underline{H}$CH$_3$), 3.75–4.20(2H, m, OC$\underline{H}_2$), 4.25–4.70(1H, m, C$\underline{H}$NH), 5.05–5.55(3H, m, N$\underline{H}$, N$\underline{H}_2$), 6.45–6.70(3H, m, C$_6\underline{H}_3$) |
| 5 | 1590 | 0.91(3H, t, J=8.1Hz, CH$_2$C$\underline{H}_3$), 1.21(3H, d, J=7.2Hz, CH$_2$CHC$\underline{H}_3$) 1.36(3H, d, J=7.2Hz, CHC$\underline{H}_3$), 1.30–1.95(2H, m, C$\underline{H}_2$CH$_3$), 2.29(6H, s, ArC$\underline{H}_3$×2), 2.20–2.70(1H, m, CH$_2$C$\underline{H}$CH$_3$) 3.70–4.20(2H, m, OC$\underline{H}_2$), 4.25–4.65 (1H, m, C$\underline{H}$NH), 5.00–5.50(3H, m, N$\underline{H}$, m, C$_6\underline{H}_3$) |
| 6*$^4$ | 1570 | 1.28(9H, s, CC$\underline{H}_3$×3), 1.34(3H, d, J=7.2Hz, CHC$\underline{H}_3$), 2.28(6H, s, ArC$\underline{H}_3$×2), 3.75–4.20(2H, m, OC$\underline{H}_2$), 4.25–4.65(1H, m, C$\underline{H}$NH), 5.10–5.50(3H, m, N$\underline{H}$, N$\underline{H}_2$), 6.45–6.70(3H, m, C$_6\underline{H}_3$) |
| 7 | 1560 | 0.97(6H, d, J=6.3Hz, C$\underline{H}_3$CHC$\underline{H}_3$), 1.36(3H, d, J=7.2Hz, CHC$\underline{H}_3$) 2.00–2.40(3H, m, C$\underline{H}_2$C$\underline{H}$), 2.30(6H, s, ArC$\underline{H}_3$×2), 3.80–4.15(2H, m, OC$\underline{H}_2$), 4.20–4.65 (1H, m, C$\underline{H}$NH), 5.05–5.50(3H, m, N$\underline{H}$, N$\underline{H}_2$), 6.45–6.70(3H, m, C$_6\underline{H}_3$) |
| 8 | 1555 | 0.90(3H, t, J=7.2Hz, CH$_2$C$\underline{H}_3$), 1.36(3H, d, J=7.2Hz, CHC$\underline{H}_3$), 1.10–1.50(4H, m, C$\underline{H}_2$C$\underline{H}_2$CH$_3$), 1.50–1.95(2H, m, Triazine-CH$_2$C$\underline{H}_2$), 2.26(6H, s, ArC$\underline{H}_3$×2), 2.25–2.65(2H, m, Triazine-C$\underline{H}_2$), 3.70–4.15(2H, m, OC$\underline{H}_2$), 4.20–4.70(1H, m, C$\underline{H}$NH), 5.10–5.60(3H, m, N$\underline{H}$, N$\underline{H}_2$), 6.40–6.70(3H, m, C$_6\underline{H}_3$) |
| | (No. 2) | |
| 9 | 1555 | 1.36(3H, d, J=7.2Hz, CHC$\underline{H}_3$), 1.15–2.10 (10H, m, C$\underline{H}_2$×5), 2.27(6H, s, ArC$\underline{H}_3$×2), 2.35–2.60 (1H, m, Triazine-C$\underline{H}$), 3.75–4.15(2H, m, OC$\underline{H}_2$), 4.20–4.70 (1H, m, C$\underline{H}$NH), 5.00–5.50(3H, m, N$\underline{H}$, N$\underline{H}_2$), 6.40–6.70 (3H, m, C$_6\underline{H}_3$) |
| 10 | 1575 | 1.36(3H, d, J=7.2Hz, CHC$\underline{H}_3$), 1.42(3H, d, J=8.1Hz, C$\underline{H}_3$CHO), 2.26(6H, s, ArC$\underline{H}_3$×2), 3.36(3H, s, OC$\underline{H}_3$), 3.80–4.15(2H, m, OC$\underline{H}_2$), 3.95–4.20(1H, m, OC$\underline{H}$), 4.20–4.70(1H, m, C$\underline{H}$NH), |

TABLE 2-continued

| Example No. | IR (cm$^{-1}$)*1 S-triazine | $^1$H-NMR*2 |
|---|---|---|
| | | 5.35–6.15(3H, m, N<u>H</u>, N<u>H</u>$_2$), 6.40–6.70(3H, m, C$_6$<u>H</u>$_3$) |
| 11 | 1570 | 0.98(3H, t, J=6.3Hz, CH$_2$C<u>H</u>$_3$), 1.36(3H, d, J=7.2Hz, CHC<u>H</u>$_3$), 1.55–2.10(2H, m, C<u>H</u>$_2$CH$_3$), 2.27(6H, s, ArC<u>H</u>$_3$×2), 3.36(3H, s, OC<u>H</u>$_3$), 3.65–4.00(1H, m, OC<u>H</u>), 3.75–4.15(2H, m, OC<u>H</u>$_2$), 4.20–4.70(1H, m, C<u>H</u>NH), 5.20–5.70(3H, m, N<u>H</u>, N<u>H</u>$_2$), 6.40–6.70(3H, m, C$_6$<u>H</u>$_3$) |
| 12 | 1565 | 1.20(3H, t, J=7.2Hz, CH$_2$CHC<u>H</u>$_3$), 1.35(3H, d, J=7.2Hz, CHC<u>H</u>$_3$) 2.29(6H, s, ArC<u>H</u>$_3$×2), 2.70–3.10(1H, m, Triazine-C<u>H</u>), 3.20–3.80(2H, m, CH$_3$OC<u>H</u>$_2$), 3.34(3H, s, OC<u>H</u>$_3$), 3.80–4.15(2H, m, OC<u>H</u>$_2$), 4.20–4.65(1H, m, C<u>H</u>NH), 5.10–5.60(3H, m, N<u>H</u>, N<u>H</u>$_2$), 6.40–6.70(3H, m, C$_6$<u>H</u>$_3$) |
| 13 | 1555 | 1.37(3H, d, J=7.2Hz, CHC<u>H</u>$_3$), 1.51(6H, s, CC<u>H</u>$_3$×2), 2.28(6H, s, ArC<u>H</u>$_3$×2), 3.23(3H, s, OC<u>H</u>$_3$), 3.80–4.15(2H, m, OC<u>H</u>$_2$), 4.20–4.65(1H, m, C<u>H</u>NH), 5.35–5.90(3H, m, N<u>H</u>, N<u>H</u>$_2$), 6.40–6.70(3H, m, C$_6$<u>H</u>$_3$) |
| 14 | 1570 | 1.30(9H, s, CC<u>H</u>$_3$×3), 1.35(3H, d, J=7.2Hz, CHC<u>H</u>$_3$), 2.28(6H, s, ArC<u>H</u>$_3$×2), 3.75–4.15(2H, m, OC<u>H</u>$_2$), 4.25(2H, s, Triazine-C<u>H</u>$_2$), 4.25–4.65(1H, m, C<u>H</u>NH), 5.05–5.80(3H, m, N<u>H</u>, N<u>H</u>$_2$), 6.45–6.70(3H, m, C$_6$<u>H</u>$_3$) |
| 15 | 1570 | 1.35(3H, d, J=7.2Hz, CHC<u>H</u>$_3$), 2.29(6H, s, ArC<u>H</u>$_3$×2), 3.44(6H, s, OC<u>H</u>$_3$×2), 3.80–4.15(2H, m, OC<u>H</u>$_2$), 4.20–4.70(1H, m, C<u>H</u>NH), 5.00(1H, s, OC<u>H</u>), 5.60–6.30(3H, m, N<u>H</u>, N<u>H</u>$_2$), 6.45–6.70(3H, m, C$_6$<u>H</u>$_3$) |
| 16 | 1570 | 1.25(6H, s, CC<u>H</u>$_3$×2), 1.36(3H, d, J=7.2Hz, CHC<u>H</u>$_3$), 2.30(6H, s, ArC<u>H</u>$_3$×2), 3.62(2H, s, C<u>H</u>$_2$OH), 3.80–4.15(2H, m, OC<u>H</u>$_2$), 4.25–4.65(1H, m, C<u>H</u>NH), 4.78(1H, s, O<u>H</u>), 5.05–5.60(3H, m, NH, N<u>H</u>$_2$), 6.45–6.70(3H, m, C$_6$<u>H</u>$_3$) (No. 3) |
| 17 | 1560 | 1.38(3H, d, J=7.2Hz, CHC<u>H</u>$_3$), 1.47(6H, s, CC<u>H</u>$_3$×2), 2.30(6H, s, ArC<u>H</u>$_3$×2), 3.80–4.15(2H, m, OC<u>H</u>$_2$), 4.25–4.70(1H, m, C<u>H</u>NH), 4.69(1H, s, O<u>H</u>), 4.90–5.55(3H, m, N<u>H</u>, N<u>H</u>$_2$), 6.45–6.70(3H, m, C$_6$<u>H</u>$_3$) |
| 18 | 1560 | 0.98(3H, t, J=8.1Hz, CH$_2$C<u>H</u>$_3$), 1.37(3H, d, J=7.2Hz, CHC<u>H</u>$_3$), 1.55–2.15(2H, m, C<u>H</u>$_2$CH$_3$), 2.27(6H, s, ArC<u>H</u>$_3$×2), 3.80–4.15(3H, m, OC<u>H</u>$_3$, OCH), 4.15–4.70(2H, m, O<u>H</u>, C<u>H</u>NH), 4.90–5.60(3H, m, N<u>H</u>, N<u>H</u>$_2$), 6.40–6.70(3H, m, C$_6$<u>H</u>$_3$) |
| 19 | 1565 | 1.25(9H, s, CC<u>H</u>$_3$×3), 1.36(3H, d, J=7.2Hz, CHC<u>H</u>$_3$), 3.75–4.20(2H, m, OC<u>H</u>$_2$), 4.25–4.65(1H, m, C<u>H</u>NH), 4.90–5.40(3H, m, N<u>H</u>, N<u>H</u>$_2$), 6.40–7.40(4H, m, C$_6$<u>H</u>$_4$) |
| 20 | 1570 | 1.35(3H, d, J=7.2Hz, CHC<u>H</u>$_3$), 2.28(3H, s, Triazine-C<u>H</u>$_3$), 3.75–4.20(2H, m, OC<u>H</u>$_2$), 4.25–4.70(1H, m, C<u>H</u>NH), 5.20–5.70(3H, m, N<u>H</u>, N<u>H</u>$_2$), 6.45–7.40(4H, m, C$_6$<u>H</u>$_4$) |
| 21 | 1560 | 1.36(3H, d, J=7.2Hz, CHC<u>H</u>$_3$), 1.10–2.10(10H, m, C<u>H</u>$_2$×5), 2.10–2.60(1H, m, Triazine-C<u>H</u>), 3.75–4.20(2H, m, OC<u>H</u>$_2$), 4.20–4.80(1H, m, C<u>H</u>NH), 4.80–5.40(3H, m, N<u>H</u>, N<u>H</u>$_2$), 6.45–7.40(4H, m, C$_6$<u>H</u>$_4$) |
| 22 | 1570 | 1.26(9H, s, CC<u>H</u>$_3$×3), 1.36(3H, d, J=7.2Hz, CHC<u>H</u>$_3$), 3.80–4.20(2H, m, OC<u>H</u>$_2$), 4.30–4.80(1H, m, C<u>H</u>NH), 5.10–5.75(3H, m, N<u>H</u>, N<u>H</u>$_2$), 6.80–7.45(5H, m, C$_6$<u>H</u>$_5$) |
| 23 | 1570 | 1.27(9H, s, CC<u>H</u>$_3$×3), 1.36(3H, d, J=7.2Hz, CHC<u>H</u>$_3$), 2.33(3H, s, ArC<u>H</u>$_3$), 3.80–4.20(2H, m, OC<u>H</u>$_2$), 4.25–4.80(1H, m, CHNH), 5.05–5.65(3H, m, N<u>H</u>, N<u>H</u>$_2$), 6.60–7.25(4H, m, C$_6$<u>H</u>$_4$) |

*1Potassium bromide tablet method
*2Solvent: Deutero chloroform, Internal standard: Tetramethylsilane (TMS)
*3Melting point: 86.4° C.–88.6° C.
*4Melting point: 107.5° C.–110.3° C.

Herbicide Examples (1) Preparation of Herbicide

97 Parts by weight of talc (trade name: Zeaklite) as a carrier, 1.5 parts by weight of alkylarylsulfonic acid (trade name: Neoplex, supplied by Kao-Atlas K.K.) as a surfactant and 1.5 parts by weight of a nonionic and anionic surfactant (trade name: Sorpol 800A, supplied by Toho Chemical Co., Ltd.) were uniformly pulverized and mixed to prepare a carrier for a wettable powder.

90 Parts by weight of the above carrier for a wettable powder and 10 parts by weight of the compounds (Compounds 1 to 23) of the present invention obtained in the above Preparation Examples 1 to 23 or 10 parts by weight of one of compounds shown in the following Table 3 (comparative Compounds 1 to 4) for Comparative Examples were uniformly pulverized and mixed to obtain herbicides.

TABLE 3

| CEx. No. | Triazine Derivative | |
|---|---|---|
| 1 | [structure: 3,5-dimethylphenoxy-CH(CH3)-NH-triazine(SCH3)(NH2)] | Compound No. 31 described in JP-A-63-264465 |
| 2 | [structure: 3-methylphenoxy-CH(CH3)-NH-triazine(SCH3)(NH2)] | Compound No. 22 described in JP-A-63-264465 |
| 3 | [structure: 3,5-dimethylphenoxy-CH(CH3)-NH-triazine(CF(CH3))(NH2)] | Compound in Preparation Example 2 described in WO90/09378 |
| 4 | [structure: 3-methylphenoxy-CH(CH3)-NH-triazine(CF(CH3))(NH2)] | Compound in Preparation Example 13 described in WO90/09378 |

CEx. = Comparative Example (2) Entire Soil Surface Treatment Test—Text

Examples 1–27

Seeds of wheat and barley as crops and seeds of Persian speedwell as a weeds were sown in 1/5,000 -are Wagner pots filled with soil (Arakida soil+sand, 1:1), covered with soil and grown in a greenhouse. Water was fed from a bottom of the pot, and the water content of the soil was maintained at a saturated water content of the soil used for the test. When these plants were at the stage of 3 leaves, a predetermined amount of the herbicide prepared in the above (1) was suspended in water to prepare herbicide suspensions having six different concentrations shown in the following Table 4, and the suspensions were uniformly sprayed onto the entire soil surfaces of the pots at a rate of 500 liters/ha each. Then, the plants were grown in a greenhouse, and on 30th day after the treatment, the herbicidal was evaluated for phytotoxicity to the crops and herbicidal efficacy. The crops-weeds selectivity was calculated on the basis of the evaluation results. Table 4 shows the results.

The phytotoxcity to crops, herbicidal efficacy and crops-weeds selectivity are shown on the basis of the following ratings.

| Phytotoxicity to crops | Loss of root portion (to non-treated plot) (%) |
|---|---|
| 0 | 0 |
| 1 | 1–10 |
| 2 | 11–20 |
| 3 | 21–30 |
| 4 | 31–40 |
| 5 | 41– |

Loss of root portion (%)=(weight of root portion in treated plot/weight of root portion in non-treated plot)×100

| Herbicidal efficacy | Ratio of remaining plant weight (to non-treated plot) (%) |
|---|---|
| 0 | 81–100 |
| 1 | 61–80 |
| 2 | 41–60 |
| 3 | 21–40 |

| Herbicidal efficacy | Ratio of remaining plant weight (to non-treated plot) (%) |
|---|---|
| 4 | 1–20 |
| 5 | 0 |

The ratio of remaining plant weight to non-treated= (remaining plant weight in treated plot/remaining plant weight in non-treated plot)×100.

Selectivity

Allowable range of phytotoxicity to crops: Loss of root portion 20% or less

Selectivity=[Maximum dosage when the loss of root portion is "2"(20%) or less]/[Minimum dosage when the herbicidal efficacy is "5"]

TABLE 4

| Test Example | Compound Example | Dosage g/ha | Phytotoxicity Wheat | Phytotoxicity Barley | Herbicidal efficacy Persian Speedwell | Selectivity Wheat | Selectivity Barley |
|---|---|---|---|---|---|---|---|
| (No. 1) | | | | | | | |
| 1 | Example No. 1 | 2,000 | 2 | 2 | 5 | 16 | 16 |
| | | 1,000 | 1 | 2 | 5 | | |
| | | 500 | 1 | 1 | 5 | | |
| | | 250 | 0 | 1 | 5 | | |
| | | 125 | 0 | 1 | 5 | | |
| | | 62 | 0 | 0 | 4 | | |
| 2 | Example No. 2 | 2,000 | 2 | 2 | 5 | 8 | 8 |
| | | 1,000 | 1 | 2 | 5 | | |
| | | 500 | 1 | 1 | 5 | | |
| | | 250 | 0 | 1 | 5 | | |
| | | 125 | 0 | 1 | 4 | | |
| | | 62 | 0 | 0 | 4 | | |
| 3 | Example No. 3 | 2,000 | 2 | 2 | 5 | 16 | 16 |
| | | 1,000 | 1 | 1 | 5 | | |
| | | 500 | 1 | 1 | 5 | | |
| | | 250 | 0 | 1 | 5 | | |
| | | 125 | 0 | 1 | 5 | | |
| | | 62 | 0 | 0 | 3 | | |
| 4 | Example No. 4 | 2,000 | 2 | 2 | 5 | 16 | 16 |
| | | 1,000 | 1 | 2 | 5 | | |
| | | 500 | 1 | 2 | 5 | | |
| | | 250 | 0 | 1 | 5 | | |
| | | 125 | 0 | 1 | 5 | | |
| | | 62 | 0 | 0 | 4 | | |
| 5 | Example No. 5 | 2,000 | 2 | 2 | 5 | 16 | 16 |
| | | 1,000 | 2 | 2 | 5 | | |
| | | 500 | 1 | 1 | 5 | | |
| | | 250 | 0 | 1 | 5 | | |
| | | 125 | 0 | 1 | 5 | | |
| | | 62 | 0 | 0 | 4 | | |
| 6 | Example No. 6 | 2,000 | 2 | 2 | 5 | 16 | 16 |
| | | 1,000 | 1 | 1 | 5 | | |
| | | 500 | 1 | 1 | 5 | | |
| | | 250 | 0 | 1 | 5 | | |
| | | 125 | 0 | 0 | 5 | | |
| | | 62 | 0 | 0 | 4 | | |
| 7 | Example No. 7 | 2,000 | 2 | 2 | 5 | 16 | 16 |
| | | 1,000 | 1 | 2 | 5 | | |
| | | 500 | 1 | 1 | 5 | | |
| | | 250 | 0 | 1 | 5 | | |
| | | 125 | 0 | 1 | 5 | | |
| | | 62 | 0 | 0 | 4 | | |
| (No. 2) | | | | | | | |
| 8 | Example No. 8 | 2,000 | 2 | 2 | 5 | 8 | 8 |
| | | 1,000 | 1 | 2 | 5 | | |
| | | 500 | 1 | 1 | 5 | | |
| | | 250 | 0 | 1 | 5 | | |
| | | 125 | 0 | 1 | 4 | | |
| | | 62 | 0 | 0 | 4 | | |
| 9 | Example No. 9 | 2,000 | 2 | 3 | 5 | 16 | 8 |
| | | 1,000 | 2 | 2 | 5 | | |
| | | 500 | 2 | 2 | 5 | | |
| | | 250 | 1 | 1 | 5 | | |
| | | 125 | 0 | 1 | 5 | | |

TABLE 4-continued

| Test Example | Compound Example | Dosage g/ha | Phytotoxicity Wheat | Barley | Herbicidal efficacy Persian Speedwell | Selectivity Wheat | Barley |
|---|---|---|---|---|---|---|---|
| | | 62 | 0 | 0 | 4 | | |
| 10 | Example No. 10 | 2,000 | 2 | 3 | 5 | 16 | 8 |
| | | 1,000 | 1 | 2 | 5 | | |
| | | 500 | 1 | 1 | 5 | | |
| | | 250 | 1 | 1 | 5 | | |
| | | 125 | 0 | 1 | 5 | | |
| | | 62 | 0 | 0 | 4 | | |
| 11 | Example No. 11 | 2,000 | 2 | 3 | 5 | 16 | 8 |
| | | 1,000 | 1 | 2 | 5 | | |
| | | 500 | 1 | 1 | 5 | | |
| | | 250 | 0 | 1 | 5 | | |
| | | 125 | 0 | 0 | 5 | | |
| | | 62 | 0 | 0 | 4 | | |
| 12 | Example No. 12 | 2,000 | 2 | 2 | 5 | 16 | 16 |
| | | 1,000 | 1 | 1 | 5 | | |
| | | 500 | 1 | 1 | 5 | | |
| | | 250 | 1 | 1 | 5 | | |
| | | 125 | 0 | 1 | 5 | | |
| | | 62 | 0 | 0 | 4 | | |
| 13 | Example No. 13 | 2,000 | 2 | 2 | 5 | 16 | 16 |
| | | 1,000 | 1 | 2 | 5 | | |
| | | 500 | 1 | 1 | 5 | | |
| | | 250 | 0 | 1 | 5 | | |
| | | 125 | 0 | 1 | 5 | | |
| | | 62 | 0 | 0 | 4 | | |
| 14 | Example No. 14 | 2,000 | 2 | 2 | 5 | 8 | 8 |
| | | 1,000 | 1 | 2 | 5 | | |
| | | 500 | 1 | 1 | 5 | | |
| | | 250 | 0 | 1 | 5 | | |
| | | 125 | 0 | 1 | 4 | | |
| | | 62 | 0 | 0 | 3 | | |
| | | (No. 3) | | | | | |
| 15 | Example No. 15 | 2,000 | 2 | 3 | 5 | 16 | 8 |
| | | 1,000 | 1 | 2 | 5 | | |
| | | 500 | 1 | 1 | 5 | | |
| | | 250 | 0 | 1 | 5 | | |
| | | 125 | 0 | 1 | 5 | | |
| | | 62 | 0 | 0 | 4 | | |
| 16 | Example No. 16 | 2,000 | 2 | 2 | 5 | 8 | 8 |
| | | 1,000 | 1 | 2 | 5 | | |
| | | 500 | 1 | 1 | 5 | | |
| | | 250 | 0 | 1 | 5 | | |
| | | 125 | 0 | 1 | 4 | | |
| | | 62 | 0 | 0 | 4 | | |
| 17 | Example No. 17 | 2,000 | 2 | 3 | 5 | 16 | 8 |
| | | 1,000 | 2 | 2 | 5 | | |
| | | 500 | 1 | 1 | 5 | | |
| | | 250 | 0 | 1 | 5 | | |
| | | 125 | 0 | 0 | 5 | | |
| | | 62 | 0 | 0 | 4 | | |
| 18 | Example No. 18 | 2,000 | 2 | 2 | 5 | 16 | 16 |
| | | 1,000 | 1 | 2 | 5 | | |
| | | 500 | 1 | 1 | 5 | | |
| | | 250 | 0 | 1 | 5 | | |
| | | 125 | 0 | 1 | 5 | | |
| | | 62 | 0 | 0 | 4 | | |
| 19 | Example No. 19 | 2,000 | 2 | 3 | 5 | 16 | 8 |
| | | 1,000 | 2 | 2 | 5 | | |
| | | 500 | 1 | 2 | 5 | | |
| | | 250 | 1 | 1 | 5 | | |
| | | 125 | 0 | 1 | 5 | | |
| | | 62 | 0 | 0 | 4 | | |
| 20 | Example No. 20 | 2,000 | 2 | 2 | 5 | 8 | 8 |
| | | 1,000 | 1 | 2 | 5 | | |
| | | 500 | 1 | 1 | 5 | | |
| | | 250 | 0 | 1 | 5 | | |
| | | 125 | 0 | 1 | 4 | | |
| | | 62 | 0 | 0 | 4 | | |
| 21 | Example No. 21 | 2,000 | 2 | 2 | 5 | 16 | 16 |
| | | 1,000 | 1 | 2 | 5 | | |
| | | 500 | 1 | 1 | 5 | | |
| | | 250 | 0 | 1 | 5 | | |

TABLE 4-continued

| Test Example | Compound Example | Dosage g/ha | Phytotoxicity | | Herbicidal efficacy Persian Speedwell | Selectivity | |
|---|---|---|---|---|---|---|---|
| | | | Wheat | Barley | | Wheat | Barley |
| | | 125 | 0 | 1 | 5 | | |
| | | 62 | 0 | 0 | 4 | | |
| | | (No. 4) | | | | | |
| 22 | Example No. 22 | 2,000 | 2 | 2 | 5 | 16 | 16 |
| | | 1,000 | 1 | 1 | 5 | | |
| | | 500 | 1 | 1 | 5 | | |
| | | 250 | 0 | 1 | 5 | | |
| | | 125 | 0 | 1 | 5 | | |
| | | 62 | 0 | 0 | 4 | | |
| 23 | Example No. 23 | 2,000 | 2 | 2 | 5 | 16 | 16 |
| | | 1,000 | 1 | 2 | 5 | | |
| | | 500 | 1 | 2 | 5 | | |
| | | 250 | 1 | 1 | 5 | | |
| | | 125 | 1 | 1 | 5 | | |
| | | 62 | 0 | 0 | 4 | | |
| 24 | Comparative Example No. 1 | 2,000 | 2 | 3 | 5 | 4 | 2 |
| | | 1,000 | 2 | 2 | 5 | | |
| | | 500 | 1 | 1 | 5 | | |
| | | 250 | 1 | 1 | 4 | | |
| | | 125 | 0 | 0 | 3 | | |
| | | 62 | 0 | 0 | 1 | | |
| 25 | Comparative Example No. 2 | 2,000 | 2 | 3 | 5 | 4 | 2 |
| | | 1,000 | 1 | 2 | 5 | | |
| | | 500 | 1 | 1 | 5 | | |
| | | 250 | 0 | 1 | 3 | | |
| | | 125 | 0 | 1 | 2 | | |
| | | 62 | 0 | 0 | 1 | | |
| 26 | Comparative Example No. 3 | 2,000 | 3 | 3 | 5 | 4 | 4 |
| | | 1,000 | 3 | 3 | 5 | | |
| | | 500 | 2 | 2 | 5 | | |
| | | 250 | 1 | 2 | 5 | | |
| | | 125 | 1 | 1 | 5 | | |
| | | 62 | 0 | 1 | 4 | | |
| 27 | Comparative Example No. 4 | 2,000 | 3 | 3 | 5 | 4 | 4 |
| | | 1,000 | 2 | 2 | 5 | | |
| | | 500 | 1 | 2 | 5 | | |
| | | 250 | 0 | 1 | 5 | | |
| | | 125 | 0 | 1 | 4 | | |
| | | 62 | 0 | 0 | 3 | | |

The results of Table 4 clearly show that the crops-weeds selectivity of the herbicides of the present invention in the entire soil surface treatment against Persian speedwell which is difficult to control is as high as 8 to 16 as compared with the crops-weeds selectivity of 2 to 4 in Comparative Examples and that the herbidices of the present invention have remarkably excellent crops-weeds selectivity even under the condition of an excessive water content which is liable to cause phytotoxicity.

(3) Entire Soil Surface Treatment Test 2—Text

Examples 28 to 33

The treatment in the above entire soil surface treatment test 1 was repeated except that the Persian speedwell used in the entire soil surface treatment test 1 in the above (2) was replaced with violet, knotweed and cleavers. On the 30th day after the treatment with the herbicides, the herbicides were evaluated for phytotoxicity to the crops and the herbicidal efficacy. The crops-weeds selectivity was calculated on the basis of the results thereof. Table 5 shows the results.

The phytotoxicity to the crops, the herbicidal efficacy and the crops-weeds selectivity are shown or were calculated on the ratings shown in the above (2).

TABLE 5

| Test Ex. | Compound Ex. | Dosage g/ha | Phytotoxicity | | Herbicidal efficacy | | | Selectivity | | |
|---|---|---|---|---|---|---|---|---|---|---|
| | | | Wheat | Barley | A | B | C | A | B | C |
| (No. 1) | | | | | | | | | | |
| 28 | Ex. | 2,000 | 2 | 2 | 5 | 5 | 5 | Wheat | | |
| | No. 4 | 1,000 | 1 | 2 | 5 | 5 | 5 | 32 | 32 | 16 |
| | | 500 | 1 | 2 | 5 | 5 | 5 | Barley | | |
| | | 250 | 0 | 1 | 5 | 5 | 5 | 32 | 32 | 16 |
| | | 125 | 0 | 1 | 5 | 5 | 5 | | | |
| | | 62 | 0 | 0 | 5 | 5 | 4 | | | |
| 29 | Ex. | 2,000 | 2 | 2 | 5 | 5 | 5 | Wheat | | |
| | No. 6 | 1,000 | 1 | 1 | 5 | 5 | 5 | 32 | 32 | 16 |
| | | 500 | 1 | 1 | 5 | 5 | 5 | Barley | | |
| | | 250 | 0 | 1 | 5 | 5 | 5 | 32 | 32 | 16 |
| | | 125 | 0 | 0 | 5 | 5 | 5 | | | |
| | | 62 | 0 | 0 | 5 | 5 | 4 | | | |
| 30 | Ex. | 2,000 | 2 | 2 | 5 | 5 | 5 | Wheat | | |
| | No. 13 | 1,000 | 1 | 2 | 5 | 5 | 5 | 32 | 32 | 16 |
| | | 500 | 1 | 1 | 5 | 5 | 5 | Barley | | |
| | | 250 | 0 | 1 | 5 | 5 | 5 | 32 | 32 | 16 |
| | | 125 | 0 | 1 | 5 | 5 | 5 | | | |
| | | 62 | 0 | 0 | 5 | 5 | 4 | | | |
| (No. 2) | | | | | | | | | | |
| 31 | Ex. | 2,000 | 2 | 3 | 5 | 5 | 5 | Wheat | | |
| | No. 19 | 1,000 | 2 | 2 | 5 | 5 | 5 | 32 | 32 | 16 |
| | | 500 | 1 | 2 | 5 | 5 | 5 | Barley | | |
| | | 250 | 1 | 1 | 5 | 5 | 5 | 16 | 16 | 8 |
| | | 125 | 0 | 1 | 5 | 5 | 5 | | | |
| | | 62 | 0 | 0 | 5 | 5 | 4 | | | |
| 32 | CEx. | 2,000 | 2 | 3 | 5 | 5 | 5 | Wheat | | |
| | No. 1 | 1,000 | 2 | 2 | 5 | 5 | 5 | 4 | 4 | 4 |
| | | 500 | 1 | 1 | 5 | 5 | 5 | Barley | | |
| | | 250 | 1 | 1 | 4 | 4 | 3 | 2 | 2 | 2 |
| | | 125 | 0 | 0 | 4 | 3 | 2 | | | |
| | | 62 | 0 | 0 | 3 | 2 | 1 | | | |
| 33 | CEx. | 2,000 | 3 | 3 | 5 | 5 | 5 | Wheat | | |
| | No. 3 | 1,000 | 3 | 3 | 5 | 5 | 5 | 8 | 8 | 4 |
| | | 500 | 2 | 2 | 5 | 5 | 5 | Barley | | |
| | | 250 | 1 | 2 | 5 | 5 | 5 | 8 | 8 | 4 |
| | | 125 | 1 | 1 | 5 | 5 | 5 | | | |
| | | 62 | 0 | 1 | 5 | 5 | 4 | | | |

Ex = Example, CEx. = Comparative Example
A = Violet, B = Knotweed, C = Cleavers

The results of Table 5 clearly show that the crops-weeds selectivity of the herbicides of the present invention in the entire soil surface treatment against violet, knotweed and cleavers which are difficult to control is as high as 16 to 32 as compared with the crops-weeds selectivity of 2 to 8 in Comparative Examples and that the herbidices of the present invention have remarkably excellent crops-weeds selectivity even under the condition of an excessive water content which is liable to cause phytotoxicity.

Industrial Utility

According to the present invention, there are provided novel triazine derivatives which show excellent crops-weeds selectivity under the condition of an excessive water content which is liable to cause phytotoxicity, a process for the production thereof, novel herbicides containing them as active ingredients, and a method of controlling weeds with them.

What is claimed is:

1. A triazine compound of the formula (I),

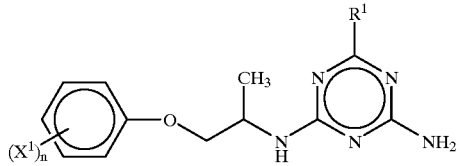

(I)

wherein

X¹ is a linear or branched $C_1$ to $C_4$ alkyl group or a halogen atom;

n is an integer of 0 or 1 to 4, provided that when n is 2 or more, a plurality of substituents X¹ are the same or different; and R¹ is a linear or branched $C_1$ to $C_{10}$ alkyl group which is unsubstituted or substituted with 1 to 4 $C_1$ to $C_4$ alkoxy groups and/or hydroxy groups, provided that when the linear or branched $C_1$ to $C_{10}$ alkyl group is substituted with 2 or more $C_1$ to $C_4$ alkoxy groups and/or hydroxy groups, a plurality of the $C_1$ to C4 alkoxy groups and/or hydroxy groups are the same or different;

or salt thereof.

2. The compound of claim 1, wherein X¹ is methyl or fluorine atom.

3. The compound of claim 2, wherein n is 0, 1 or 2.

4. The compound of claim 3, wherein n is 1 or 2, substituent(s) X¹ is/are substituted on the 3-position and/or the 5-position on the phenoxy group.

5. The compound of claim 1, wherein R¹ is a linear or branched $C_1$ to $C_8$ alkyl group which is unsubstituted or substituted with 1 to 4 $C_1$ to $C_4$ alkoxy and/or hydroxy groups.

6. The compound of claim 5, wherein R¹ is a non-substituted linear or branched $C_1$ to $C_6$ alkyl group.

7. The compound of claim 5, wherein R¹ is a linear or branched $C_1$ to $C_4$ alkyl group on which 1 or 2 $C_1$ to $C_4$ alkoxy groups are substituted or a linear or branched $C_1$ to $C_4$ alkyl group on which one hydroxy group is substituted.

8. The compound of claim 7, wherein R¹ is a linear or branched $C_1$ to $C_4$ alkyl group on which 1 or 2 methoxy groups, one butoxy group or one hydroxy group is substituted.

9. The triazine compound of claim 1, wherein the compound is selected from the group consisting of

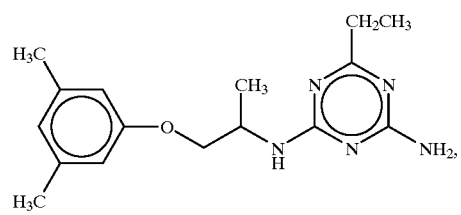

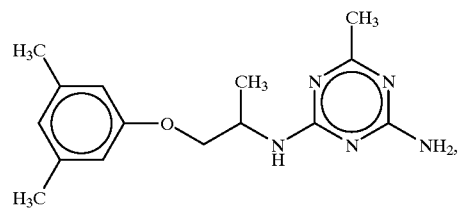

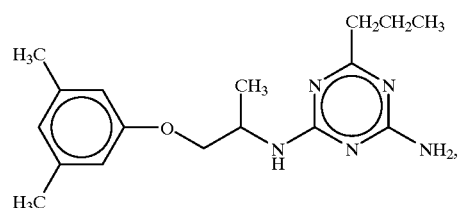

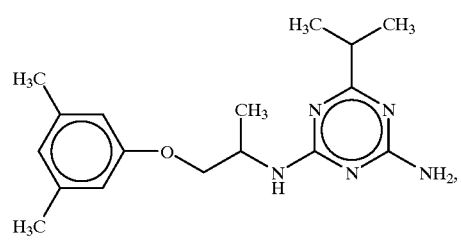

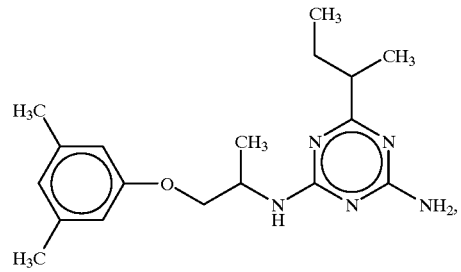

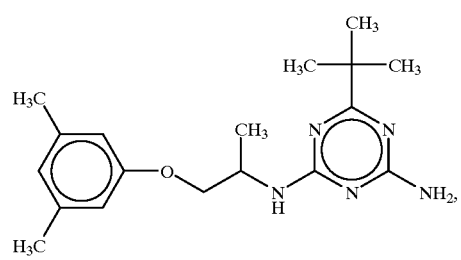

33
-continued
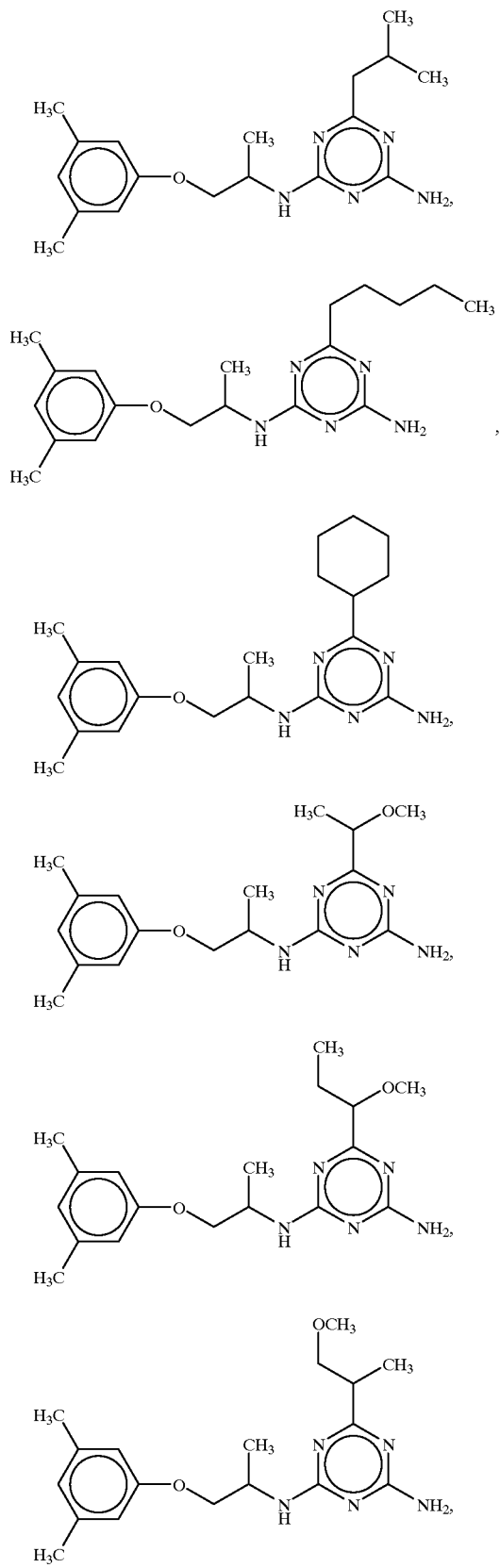
34
-continued
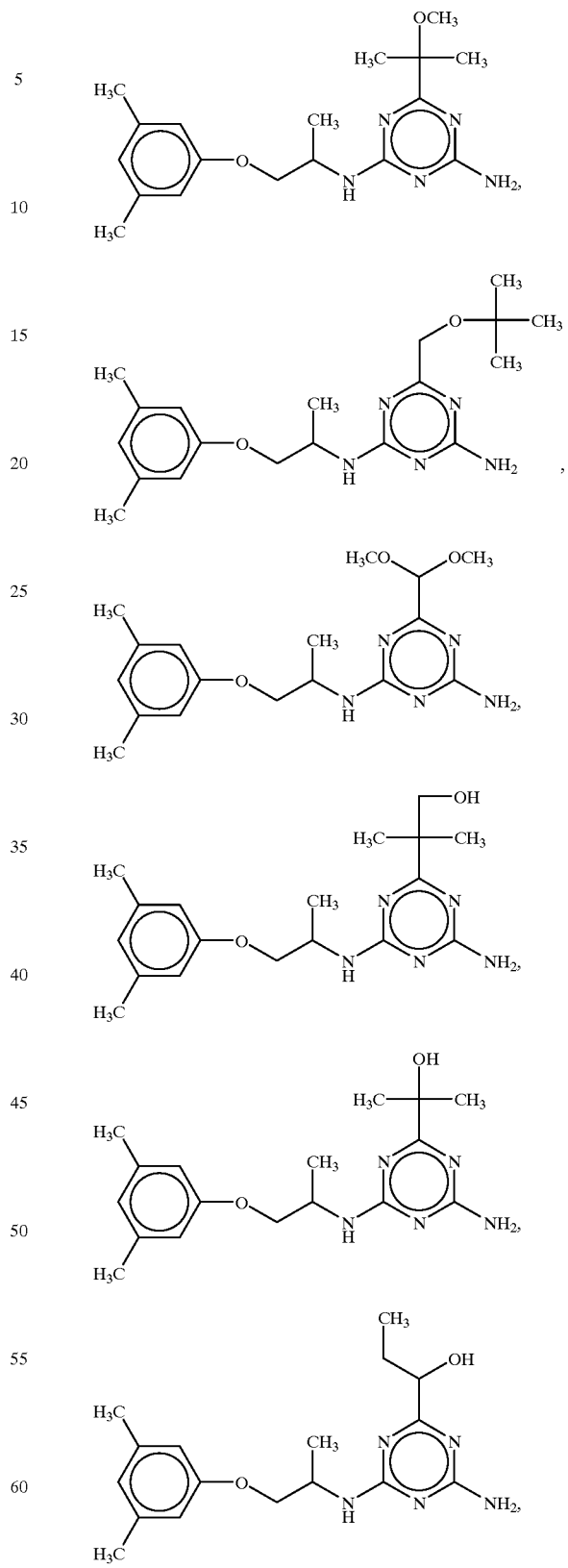

-continued

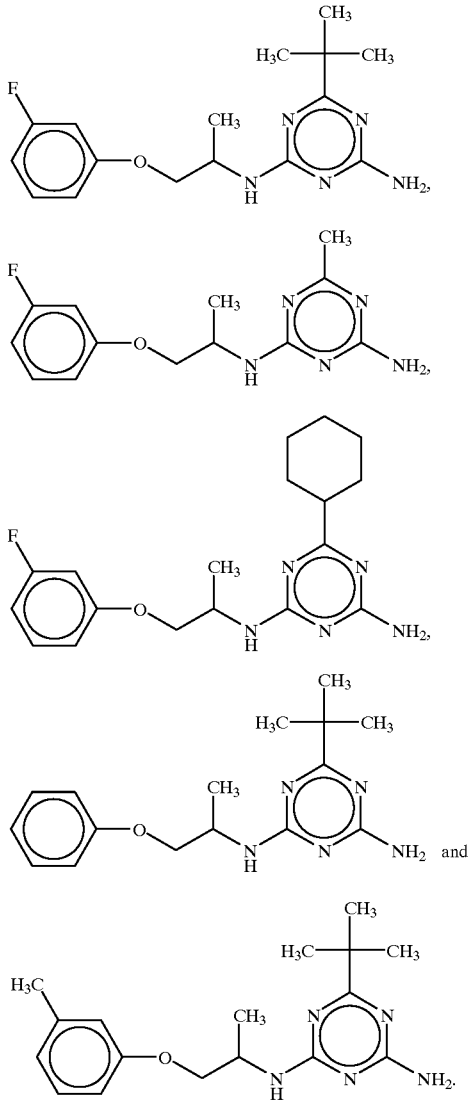

10. A process for the production of a triazine compound of the formula (I) of claim 1,

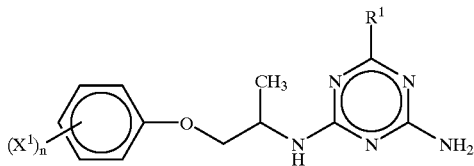

wherein
X¹ is a linear or branched $C_1$ to $C_4$ alkyl group or a halogen atom;
n is an integer of 0 or 1 to 4, provided that when n is an integer of 2 or more, a plurality of substituents X¹ are the same or different; and
R¹ is a linear or branched $C_1$ to $C_{10}$ alkyl group which is unsubstituted or substituted with 1 to 4 alkoxy groups and/or hydroxy groups, provided that when the linear or branched $C_1$ to $C_{10}$ alkyl group is substituted with 2 or more $C_1$ to $C_4$ alkoxy groups and/or hydroxyl groups, a plurality of the $C_1$ to $C_4$ alkoxy groups and/or hydroxy groups are the same or different,
which process comprises reacting a salt of an alkylbiguanide of the formula (II),

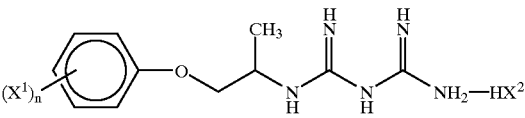

wherein X¹ and n are as defined above and X² is a halogen atom,
with an ester of the formula (III),
$$R^1COOR^2 \qquad (III)$$
wherein R¹ is as defined above and R² is a $C_1$ to $C_4$ alkyl group.

11. The process of claim 10, wherein the reaction is carried out in the presence of a dehydrating agent.

12. A herbicide composition comprising, as an active ingredient, a herbicidally effective amount of the triazine compound or salt thereof recited in any one of claims 1 to 8, in combination with a carrier or an adjuvant.

13. A method of controlling weeds, which comprises applying a herbicidally effective amount of the triazine compound or salt thereof recited in any one of claims 1 to 8, alone or together with a carrier or an adjuvant, to weeds or a locus thereof.

14. The method of claim 13, which is for controlling weeds in the cultivation of gramineous plants.

* * * * *